United States Patent
Baker et al.

(10) Patent No.: US 6,551,353 B1
(45) Date of Patent: Apr. 22, 2003

(54) SYNTHETIC FIBERS FOR MEDICAL USE AND METHOD OF MAKING THE SAME

(75) Inventors: William R. Baker, Indialantic, FL (US); William H. Hills, Melbourne Village, FL (US); Arnold E. Wilkie, Merritt Island, FL (US)

(73) Assignee: Hills, Inc., West Melbounre, FL (US)

( * ) Notice: Subject to any disclaimer, the term of this patent is extended or adjusted under 35 U.S.C. 154(b) by 0 days.

(21) Appl. No.: 09/530,183

(22) PCT Filed: Oct. 28, 1998

(86) PCT No.: PCT/US98/22810

§ 371 (c)(1),
(2), (4) Date: Apr. 26, 2000

(87) PCT Pub. No.: WO99/21507

PCT Pub. Date: May 6, 1999

Related U.S. Application Data

(60) Provisional application No. 60/065,345, filed on Oct. 28, 1997.

(51) Int. Cl.[7] ............................. A61F 2/04; D01F 8/00
(52) U.S. Cl. .................... 623/1.42; 425/373; 623/23.72
(58) Field of Search .............................. 623/1.42, 1.44, 623/1.15, 1.46, 1.47, 1.48, 23.72; 428/373, 370, 374, 397

(56) References Cited

U.S. PATENT DOCUMENTS

| | | |
|---|---|---|
| 3,978,203 A | 8/1976 | Wise |
| 3,991,766 A | 11/1976 | Schmitt et al. |
| 4,024,871 A | 5/1977 | Stephenson |
| 4,307,723 A * | 12/1981 | Finney ...................... 623/1.42 |
| 4,841,968 A | 6/1989 | Dunn et al. |
| 5,010,167 A | 4/1991 | Ron et al. |
| 5,162,074 A * | 11/1992 | Hills ........................... 216/83 |
| 5,370,681 A * | 12/1994 | Herweck .................... 623/1.42 |
| 5,378,540 A | 1/1995 | Olson |
| 5,411,550 A * | 5/1995 | Herweck .................... 623/1.42 |
| 5,551,954 A | 9/1996 | Buscemi et al. |
| 5,795,318 A * | 8/1998 | Wang ......................... 623/1.42 |
| 5,891,108 A * | 4/1999 | Leone ........................ 623/1.43 |
| 6,004,346 A * | 12/1999 | Wolff ......................... 623/1.42 |
| 6,071,305 A * | 6/2000 | Brown ....................... 623/1.42 |
| 6,206,915 B1 * | 3/2001 | Fagan ........................ 623/1.42 |
| 6,240,616 B1 * | 6/2001 | Yan ............................ 623/1.42 |
| 6,465,095 B1 * | 10/2002 | Dugan ....................... 428/373 |

* cited by examiner

Primary Examiner—David J. Isabella

(57) ABSTRACT

A synthetic fiber is formed with a plurality of longitudinally-extending cavities (16, 54 and 64) which hold a medicament that is intended to be absorbed into tissue brought into contact with the fiber. The fiber can be formed by dissolving a soluble polymer component 14 of an extruded plural-component fiber 10, leaving cavities 16 that extend inward from the outer surface of the fiber in the locations of the dissolved polymer. After the fiber has been exposed to a solvent, the cavities left by the dissolved component are filled with a medicament 18. Specifically, the cavities are filled with a medicament that is mixed with a viscous carrier which solidifies within the cavities. The fibers can be used to make sutures, textile prostheses for insertion into the body, and epidermal pads and bandages. Fibers having internal cavities 64, i.e., cavities not extending to the external surface of the fiber, can be formed by extruding a single-component fiber 60 from a spinneret orifice 72 having a number of T-shaped slots extending from a central hub. A medicament is introduced into the internal cavities by soaking the fiber in a liquid containing the medicament. The internal-cavity fiber is therefore formed of polymer having some capability for liquid transport, e.g., nylon.

7 Claims, 2 Drawing Sheets

SYNTHETIC FIBERS FOR MEDICAL USE AND METHOD OF MAKING THE SAME

CROSS REFERENCE TO RELATED APPLICATION

This application claims priority from U.S. Provisional Patent Application Ser. No. 60/065,345, entitled "Synthetic Fibers For Medical Use," filed Oct. 28, 1997. The disclosure of that provisional patent application is incorporated herein by reference in its entirety.

BACKGROUND OF THE INVENTION

1. Field of the Invention

The present invention relates to synthetic fibers for medical use and methods for making such synthetic fibers, and, more particularly, to synthetic fibers having cavities adapted to hold relatively large quantities of a medicament, for use in forming sutures, textile prostheses and medicated epidermal pads.

2. Description of the Related Art

Conventionally, synthetic fibers useful for medical applications such as sutures, textile prosthesis, and medicated pads that are applied to the skin, have been fabricated as solid fibers that carry a medicament. For example, U.S. Pat. No. 3,978,203 to Wise, incorporated herein by reference in its entirety, discloses medicine-bearing, polymer-based products, such as sutures and matrices formed in predetermined shapes for bodily implantation, which control the rate at which the medicine is released into the surrounding tissue.

U.S. Pat. No. 3,991,766 to Schmitt et al., incorporated herein by reference in its entirety, discloses absorbable surgical elements, such as sutures, clips, sponges, gauze, prosthetic devices, and storage pellets having medicaments incorporated therein which are released into tissue over time as the surgical element is absorbed. The medicament is combined with a base material of polyglycolic acid (PGA) and subsequently formed into the surgical elements, e.g., by being spun into filaments to form sutures.

Similarly, U.S. Pat. No. 5,010,167 to Ron et al., incorporated herein by reference in its entirety, discloses biocompatible, biodegradable polymers useful for making controlled release devices for drug delivery, such as bioabsorbable sutures, wherein the drug is incorporated directly into the polymer.

U.S. Pat. No. 4,024,871 to Stevenson, incorporated herein by reference in its entirety, discloses multifilament suture stands that are impregnated with an antimicrobial agent and top coated with a segmented polymer, such that the sutures retain antimicrobial properties over an extended period of time. The antimicrobial agent is distributed substantially throughout the suture in the interstices between strands and between individual filaments.

U.S. Pat. No. 5,378,540 to Olson, incorporated herein by reference in its entirety, discloses coating an absorbable braided suture with a solution that controls the release of chemical or pharmaceutical agents as the suture is absorbed into living tissue.

U.S. Pat. No. 4,841,968 to Dunn et al., incorporated herein by reference in its entirety, discloses biodegradable sutures having a core and sheath configuration, wherein the core comprises a blend of a polymer and an agent to be released into living tissue, and the sheath comprises only the polymer.

While these known synthetic fibers are effective in controlling the release rate of a medicament into tissue, these fibers are either solid fibers that require the medicine to be absorbed into the fiber or fibers comprising medicine intermixed with a polymer prior to extrusion and formation of the fibers from the mixture. Consequently, these fibers have a limited capacity to hold medicine. Accordingly, there remains a need for synthetic fibers useful for forming sutures, textile prostheses, medicated epidermal pads, and the like, that have the capacity to hold more medicine than conventional synthetic fibers.

SUMMARY OF THE INVENTION

It is an object of the present invention to provide synthetic fibers useful for forming sutures, textile prostheses and medicated epidermal pads, that are capable of holding a greater quantity of medicine than conventional synthetic fibers.

It is another object of the present invention to employ bicomponent fiber extrusion techniques to form synthetic fibers capable of storing medicine to be released into living tissue.

It is a yet another object of the present invention to provide for storage of medicine, to be time released into the body, in cavities formed in a synthetic fiber.

It is a further object of the present invention to employ single-component fiber extrusion techniques to form synthetic fibers capable of storing medicine to be released into living tissue.

The aforesaid objects are achieved individually and in combination, and it is not intended that the present invention be construed as requiring two or more of the objects to be combined unless expressly required by the claims attached hereto.

According to the present invention, a synthetic fiber is formed with a plurality of longitudinally-extending cavities which hold a medicament intended to be absorbed into living tissue brought into contact with the fiber. The fiber can be formed by dissolving a soluble polymer component of an extruded plural-component fiber, leaving cavities that extend inward from the outer surface of the fiber in the locations of the dissolved polymer. After the fiber has been exposed to a solvent, the cavities left by the dissolved component are filled with a medicament. Specifically, the cavities are filled with a medicament that is mixed with a viscous carrier which solidifies within the cavities. The fibers can be used to make sutures, textile prostheses for insertion into the body, and epidermal pads and bandages.

Fibers having internal cavities, i.e., cavities not extending to the external surface of the fiber, can be formed by extruding a single-component fiber from a spinneret orifice having a number of T-shaped slots extending from a central hub. A medicament is introduced into the internal cavities by soaking the fiber in a liquid containing the medicament. The internal-cavity fiber is therefore formed of polymer having some capability for liquid transport, e.g., nylon. A fiber with external cavities can be formed from a similar process by modifying one or more of the extrusion parameters.

Because the fiber of the present invention includes cavities or reservoirs specifically designed to hold a medicament, these fiber advantageously hold significantly more medicine that prior art fibers relying on absorption of a medicament by a fiber or formation of a polymer into which a medicament is intermixed.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

In accordance with the present invention, synthetic textile fibers, monofilaments and multifilament yarns are formed from fibers having open voids or reservoirs that can be filled with a medicament or other additives with beneficial medical uses, for subsequent absorption into the body. As used herein the terms "medicine", "medicament" and "medication" refer to any substance, agent, compound or composition of matter intended to interact with tissue or bodily fluids to treat or prevent disease or damage, cause a pharmacologic or physiologic response, or to provide some other beneficial or therapeutic effect, including, but not limited to: all types of therapeutic agents, such as antiseptics, including antibiotics, antimicrobial, antibacterial and antiviral agents, analgesics, anesthetics, anorexics, anthemidines, antiarthritics, antiasthmatic agents, anticonvulsants, antidepressants, antidiabetic agents, antidiarheals, antihistamines, antiinflammatory agents, antimigraine agents, antimotion sickness agents, antinauseants, antineoplastics, antiparkinsonism drugs, antipruitics, antipsychotics, antipyretics, antispasmodics including gastrointestinal and urinary, anticholinergics, sympathomimetics, xanthine derivatives, cardiovascular preparations including calcium channel blockers, betablockers, antiarrythmics, antihypertensives, diuretics, vasodilators, including coronary peripheral, and cerebral, central nervous stimulants, decongestants, diagnostic agents, hormones, hypnotics, immunosuppressives, muscle relaxants, parasympathomimetics, psychostimulants, sedatives, tranquilizers, agents to ease symptoms of addiction, and the like, and combinations thereof.

Figure 3:
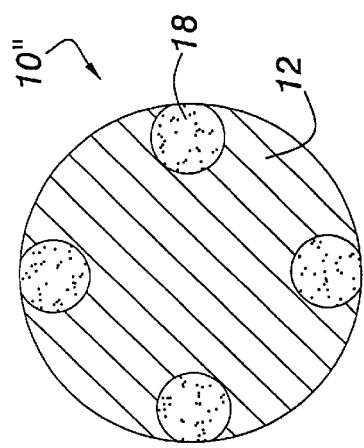
FIG. 3 is a transverse cross-sectional view of the synthetic fiber of FIG. 2, wherein the cavities are filled with a medicament in accordance with a first embodiment of the present invention.
Figure 2:
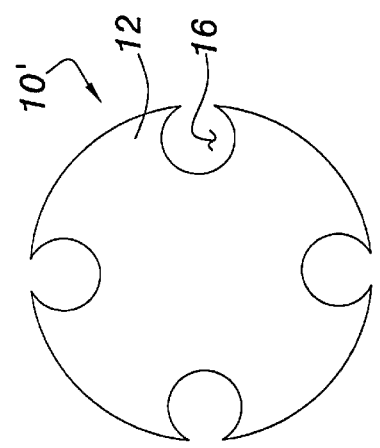
FIG. 2 is a transverse cross-sectional view of the synthetic fiber shown in FIG. 1, wherein the "island" components have been dissolved, leaving longitudinal cavities along the fiber surface, wherein the cavities have substantially round cross-sectional shapes.
Figure 1:
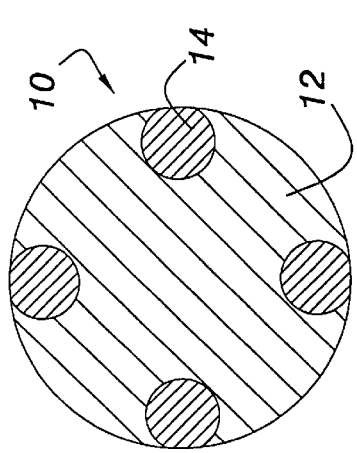
FIG. 1 is a transverse cross-sectional view of an island-in-the-sea bicomponent fiber having longitudinal "island" components along the fiber surface, wherein the "island" components are dissolvable in a solvent.

Referring to FIGS. 1–3, an extruded synthetic fiber according to an exemplary embodiment of the present invention is shown in transverse cross section at three different stages of the manufacturing process. As shown in FIG. 1, an extruded bicomponent fiber 10 is a so-called "island-in-the-sea" fiber with a substantially circular cross sectional shape. Specifically, fiber 10 comprises a durable "sea" polymer 12, which forms the bulk of fiber 10, and four polymer "islands" 14 having substantially circular cross sections. The polymer islands 14 are embedded in the sea polymer 12 and lie along the outer surface of fiber 10, spaced apart by approximately 90°, such that the islands 14 are not totally encapsulated by the sea polymer 12, and a portion of the outer surface of fiber 10 is formed by the polymer islands 14.

The sea polymer 12 of fiber 10 may be made from any organic high polymer such as nylon, polyethylene terepthalate, or polypropylene, or from absorbable polymers such as polymerized vinyl alcohol or more modem absorbable co-polymers. As used herein, the term "polymer" includes all such materials (both polymers and co-polymers). The polymer islands 14 are composed of a polymer, such as polyvinyl alcohol, which can later be dissolved in water, alcohol or another suitable solvent. Importantly, sea polymer 12 is does not dissolve in the solvent in which polymer islands 14 dissolve.

Figure 4:
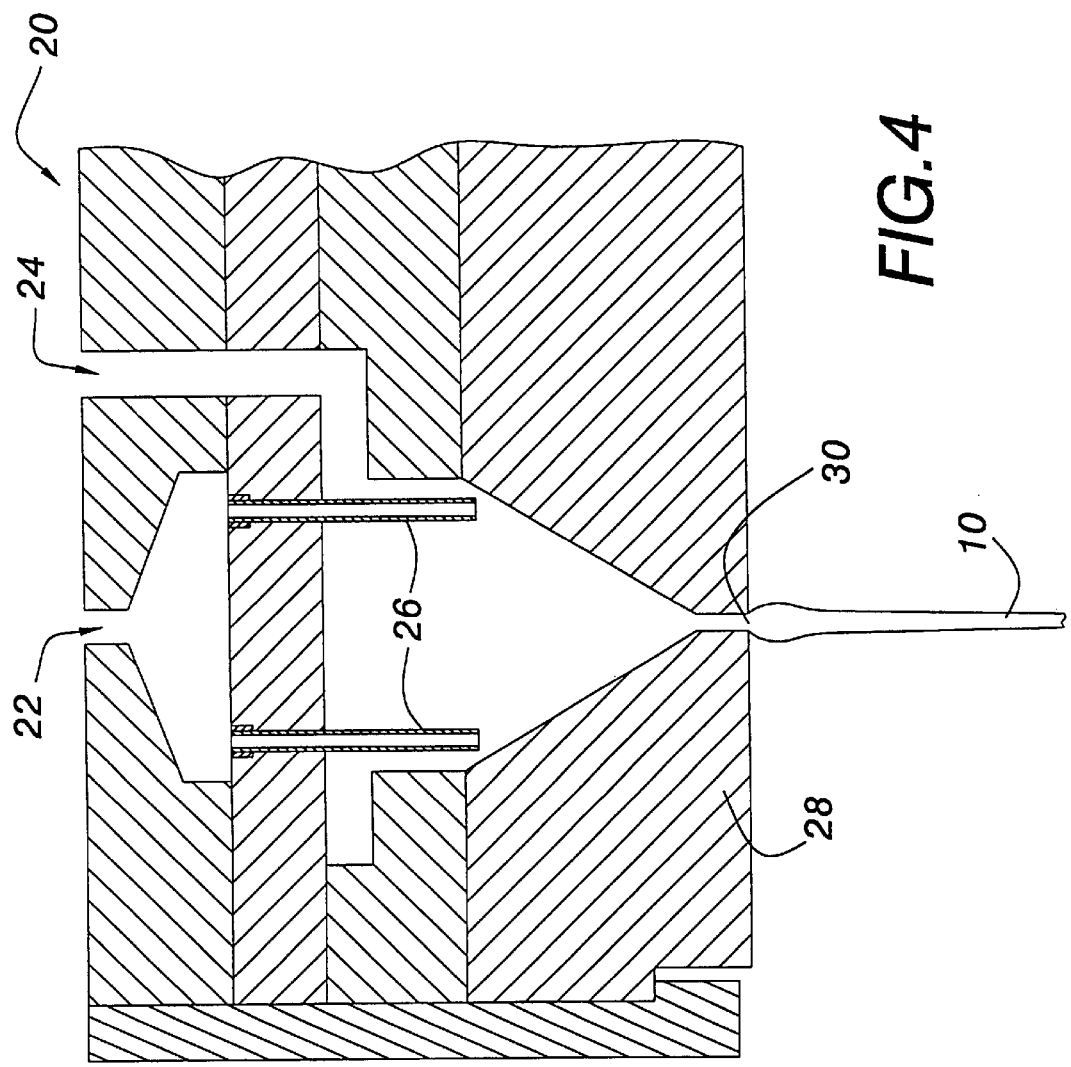
FIG. 4 is a cross-sectional view of a spin pack suitable for extruding the synthetic fiber shown in FIG. 1.

In general, the spinning of bicomponent island-in-the-sea fiber 10 shown in FIG. 1 can be by melt, dry or wet spinning. For example, bicomponent fiber 10 can be made by bicomponent spinning, using equipment of the general type disclosed in U.S. Pat. Nos. 4,370,114 or 4,381,274, the disclosures of which are incorporated herein by reference in their entirety. FIG. 4 is a cross-sectional view of a spin pack 20 that is a simplified version of the spin pack shown in FIG. 1a of U.S. Pat. No. 4,370,114 and that is suitable for generating bicomponent island-in-the-sea fiber 10. Spin pack 20 includes upstream openings 22 and 24 through which the island polymer and sea polymer respectively enter spin pack 20. The island polymer travels through capillary tubes 26 which inject the island polymer into the flow of the sea polymer at the entrance to spinneret 28 in four discrete locations along the edge of the spinneret entrance. The polymers flow through spinneret 28 to an orifice 30, where they are extruded as island-in-the-sea fiber 10.

Once bicomponent fiber 10 is formed, it is treated with a suitable solvent, such as water, to dissolve the polymer islands 14. As shown in FIG. 2, polymer islands 14 are removed by exposure to the solvent, leaving a single component (i.e., the sea polymer 12) fiber 10' having longitudinally-extending voids or cavities 16 along the surface of fiber 10' in the locations formerly occupied by the dissolved polymer islands 14. If the fibers are to be made into a fabric, it is preferable to form the fabric prior to exposure to the solvent (with the polymer islands 14 in place), and subsequently to wash the fabric in water, alcohol or some other suitable solvent to remove the polymer islands 14, leaving cavities 16 on the surface of the fibers. It will be understood that the cavities formed in the fibers of the present invention are not interstitial spaces lying between separate, adjacent polymer filaments or strands; rather, the cavities are voids formed in an otherwise solid polymer fiber.

Referring to FIG. 3, cavities 16 left along the outer surface of fiber 10' by the dissolved islands 14 serve as reservoirs that are filled with a medicament 18 to form a fiber 10". Medicament 18 can be added to the fiber by dipping the fiber (or a fabric, felt, or other textile product made from the fibers) in a bath containing the medicament in a suitable carrier. The carrier is preferable a somewhat viscous carrier so that the medicament 18 and carrier can solidify by drying and/or cooling at room temperature before the medicament/carrier can drain out of the fiber cavities.

Treating of the fibers 10' (FIG. 2) with a medicament/carrier to form fiber 10" (FIG. 3) can be performed in line with fiber extrusion or at any later time after the island polymer has been dissolved. In the latter case, sutures or fabrics made from the extruded and solvent-treated fiber 10', or fiber 10' itself, are general purpose fibers, sutures and fabrics that can be later treated with any desired medicament/carrier mixture for a particular application.

Typically, the medicament is of the type absorbed into the body over a period of time after the medical element formed from the fiber (e.g., a suture, textile prosthesis, or epidermal pad) has been deployed in or on the body.

According to another embodiment, rather than dissolving the island polymer components in a solvent, a medicament is added to the island polymer prior to fiber spinning (by melt, dry or wet spinning) to produce the desired end use fiber in one step. That is, the island polymer is extruded with the desired medicament incorporated therein, such that the extruded fiber is used directly in the final medical product without requiring the island components to be dissolved or the fiber to be dipped in a medicament/carrier mixture. Fibers produced in this manner are of a single purpose type, having a particular medicament that is predetermined at the time of extrusion.

Figure 5:
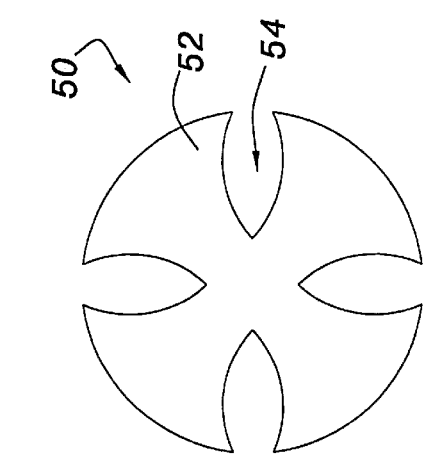
FIG. 5 is a transverse cross-sectional view of a synthetic fiber of the present invention, having longitudinal cavities along the fiber surface, wherein the cavities have cross-sectional shapes elongated in the radial direction.

The medicament-storing cavities that are formed in the fiber of the present invention need not have a circular transverse cross-sectional shape. Referring to FIG. 5, a fiber 50, having a substantially circular transverse cross-sectional profile, comprises an extruded "sea" polymer 52, with four longitudinally-extending cavities 54 created by dissolving four polymer islands that are partially embedded in the sea polymer and form part of the outer surface of the extruded fiber. The cavities 54 are spaced apart by approximately 90°, and each of cavities 54 has a substantially pointed elliptical transverse cross-section shape, with the major elliptical axis lying along a radial line. The cavities 54 extend to the outer surface of fiber 50, where the elliptical shape of the cavities is truncated. As seen in FIG. 5, the shape of cavities 54 results in sea polymer 52 having a substantially cruciform shape with the circular profile of fiber 50. Thus, fiber 50 is similar to fiber 10' (FIG. 2) except that the cavities are elongated in the radial direction. As will be evident from the fibers shown in FIGS. 1–3 and 5, the fibers of the present invention can include external (i.e., on the fiber surface) medicament-holding cavities having any of variety of different transverse cross-sectional shapes, and the present invention is not limited to the particular cross-sectional shapes shown in the figures. Further, number of cavities can be any suitable number (one or more) of external cavities.

Figure 6:
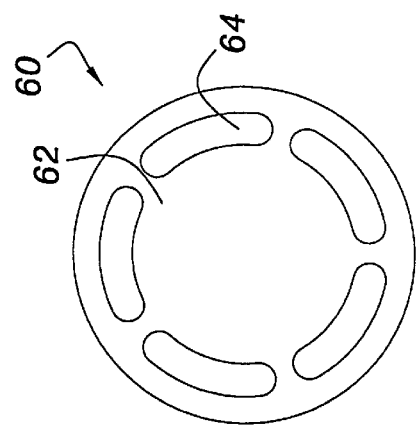
FIG. 6 is transverse cross-sectional view of a synthetic fiber of the present invention having arcuate, internal longitudinal cavities.

The fibers shown in FIGS. 1–3 and 5 have external longitudinal cavities formed into the fiber external surface; however, the present invention is not limited to fibers with external surface cavities. In accordance with another embodiment of the present invention, an extruded fiber includes one or more internal longitudinal cavities (i.e., cavities not extending to the outer surface of the fiber), which cavities lie in relatively close proximity to the fiber surface. Referring to FIG. 6, a fiber 60 having internal cavities for storing a medicament is shown. Specifically, fiber 60 has a substantially circular transverse cross-sectional profile, and comprises an extruded polymer 62 with five longitudinally-extending internal cavities 64. Each of cavities 64 has an arcuate transverse cross-section shape, and cavities 64 together form a ring of arcuate cavities lying along a circle concentric with fiber 60 (i.e., the circle lies at a fixed radial distance from the center of fiber 60).

Figure 7:
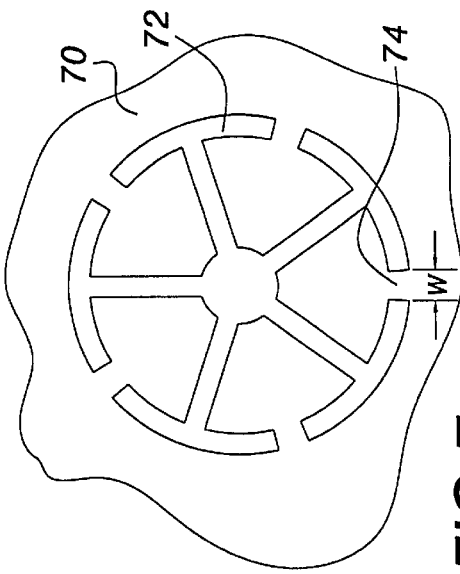
FIG. 7 is a spinneret orifice for forming a single component synthetic fiber having internal or surface longitudinal cavities for holding a medicament.

Fiber 60, and other fibers having internal cavities, can be made without the need for bicomponent spinning by employing a spinneret orifice of a suitable shape. FIG. 7 illustrates a spinneret face 70 having formed therein an orifice 72 suitable for extruding fiber 60 (FIG. 6). Orifice 72 includes five T-shaped slots extending radially outward from a circular, central hub opening. The circumferential portions of the T-shaped slots are arcuate and form an outer circular ring of openings, with gaps 74 between adjacent slots 72. If the gaps 74 between adjacent T-shaped slots are set to an appropriate width W, the polymer extruded from the T-shaped slots will bridge the gaps 74 a short distance below the spinneret, creating voids near but below the fiber surface, thereby forming a fiber having a cross-section such as that shown in FIG. 6.

A medicament can be added to fiber 60 by soaking fiber 60 in a liquid containing the medicament and, optionally, pressurizing the liquid to speed liquid transport into the fiber cavities 64. Consequently, fiber 60 is preferably made from a polymer with some capability for liquid transport, such as nylon.

Like the external-cavity fibers shown in FIGS. 1–3 and 4, the internal-cavity fiber 60 has several advantages over a simple hollow fiber with a single, central hole. Specifically, a hollow fiber with a small, single, central hole has a limited capacity to hold medicine, and transport of the medicine to the surrounding tissue is slow due to the thick fiber wall. Conversely, a hollow fiber having a large internal hole holds more medicine; however, such a fiber tends to collapse and cause processing problems in knitting, weaving or, in the case of sutures, the tying of knots.

In contrast, with the internal-cavity fiber of the present invention, because the fiber cavities are formed closer to the exterior surface of the fiber, the medicament can be transported to the surrounding tissue more rapidly than with fiber having a small, single, central cavity. Further, the medicament is distributed through several cavities, so that a large quantity of medicament can be held in the fiber without the aforementioned problems associated with fiber having a large, single, central hole.

It will be understood that the internal-cavity fiber of the present invention is not limited to the particular configuration shown in FIG. 6. For example, the cavities need not be arcuate and can have any cross-sectional shape. The cavities need not be the same size and need not lie at the same radial distance from the fiber center. Further any suitable number of internal cavities can be formed.

Referring again to FIG. 7, if the gaps 74 in the spinneret orifice 72 are made larger, if fiber cooling below the spinneret is quicker, or if the polymer is more viscous, then the polymer will not close the gaps, and a fiber somewhat similar to that shown in FIG. 2 (i.e., a fiber with external cavities) can be made without the need of bicomponent spinning. While this technique is less expensive for forming external cavities, the fiber shape can be controlled more precisely with the bicomponent "islands-in-a-sea" technique described above.

Fibers of the type described above have a variety of different medical applications and also some non-medical applications, including, but not limited to: fabrics for wound dressings and adhesive bandage pads, where the fibers contain an antiseptic or an agent to promote healing; textile prostheses where the base polymer (or copolymer) is an absorbable type and can be left to gradually disintegrate in the body, or where the base polymer is tissue-compatible and remains in the body; sutures of the absorbable or non-absorbable type made from monofilament or twisted or braided multifilaments; and patches for application to the skin where the fiber cavities contain a component such as nicotine for slow absorption into the skin.

When the cavities of the above-described fibers are not filled with medicaments, the fibers can be used in a number of non-medical applications, including, but not limited to: fibrous inking pads for rubber stamping and for the printing industry, wherein fibers such as those shown in FIGS. 2 and 5 have the longitudinal cavities filled with viscous ink; fabrics, felts or fiber masses formed from a fiber having a maximum number of empty small surface grooves and used as absorbent pads in medical or non-medical applications. Such pads can be used, for example, to absorb oil from tanker oil spills, and then wrung out and reused. Fibers such as nylon will withstand many more cycles of absorption and wringing than conventional cotton fibers used in this manner.

Having described preferred embodiments of a new and improved method and apparatus for extruding plural-component food products, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A method of fabricating a synthetic fiber for medical use, comprising the steps of:

extruding a plural-component fiber from an orifice of a spinneret;

dissolving a soluble component of the plural-component fiber in a solvent, thereby forming longitudinally-extending cavities in a remaining polymer component of the fiber; and securing a medicament in the longitudinally-extending cavities formed in the remaining polymer component of the fiber.

2. The method according to claim 1, wherein:

said extruding step includes extruding the plural-component fiber as an island-in-the-sea bicomponent fiber, wherein the soluble component forms longitudinally-extending islands in a sea component that becomes the remaining polymer component;

said dissolving step includes dissolving the soluble component forming the islands, leaving the longitudinally-extending cavities in the location of the islands; and said securing step includes filling the longitudinally-extending cavities with a mixture of the medicament and a viscous carrier, which mixture solidifies within the longitudinally-extending cavities.

3. The method according to claim 2, wherein said extruding step includes extruding the bicomponent fiber with islands that form a portion of an outer surface of the bicomponent fiber, such that said dissolving step forms the longitudinally-extending cavities as external cavities that extend inward into said remaining polymer component from an outer surface of said remaining polymer component.

4. The method according to claim 3, wherein said dissolving step produces longitudinally-extending cavities having a substantially circular transverse cross-sectional shape.

5. The method according to claim 3, wherein said dissolving step produces longitudinally-extending cavities that have a transverse cross-sectional shape that is elongated in a radial direction.

6. The method according to claim 1, wherein said extruding step includes extruding the fiber with a substantially circular transverse cross-sectional shape.

7. The method according to claim 1, wherein said extruding step includes extruding a plural-component fiber comprising at least one of: an organic high polymer such as nylon, polyethylene terepthalate, and polypropylene; an absorbable polymer such as polymerized vinyl alcohol; and a co-polymer.

* * * * *